(12) United States Patent
Franzoni et al.

(10) Patent No.: US 8,394,321 B2
(45) Date of Patent: Mar. 12, 2013

(54) MEDICAL FLUID CIRCUIT COMPRISING A LOW LEVEL DETECTOR 1

(75) Inventors: Giuseppe Franzoni, Sassuolo (IT); Luca Caleffi, Carpi (IT); Ranko Sakota, Giugliano in Campania (IT)

(73) Assignee: Gambro Lundia AB, Lund (SE)

( * ) Notice: Subject to any disclaimer, the term of this patent is extended or adjusted under 35 U.S.C. 154(b) by 128 days.

(21) Appl. No.: 12/992,540

(22) PCT Filed: Apr. 27, 2009

(86) PCT No.: PCT/IB2009/005388
§ 371 (c)(1),
(2), (4) Date: Nov. 12, 2010

(87) PCT Pub. No.: WO2009/147478
PCT Pub. Date: Dec. 10, 2009

(65) Prior Publication Data
US 2011/0064612 A1    Mar. 17, 2011

(30) Foreign Application Priority Data
May 27, 2008  (IT) .............................. MO2008A0159

(51) Int. Cl.
A61M 5/00  (2006.01)
A61M 5/142  (2006.01)
A61M 5/36  (2006.01)

(52) U.S. Cl. ................ 422/44; 604/31; 604/65; 604/66; 604/93.01; 604/118; 604/122; 604/123; 604/131; 604/151

(58) Field of Classification Search .................... 422/44, 422/48; 604/4.01, 5.01, 6.06, 6.09, 6.11, 604/63, 31, 65, 67; 340/612, 613, 614, 618, 340/626; 137/403; 73/291, 296, 299, 301, 73/302, 304 R, 304 C
See application file for complete search history.

(56) References Cited

U.S. PATENT DOCUMENTS

| | | | |
|---|---|---|---|
| 4,530,696 A | | 7/1985 | Bisera et al. |
| 4,832,689 A | * | 5/1989 | Mauerer et al. ................. 604/67 |
| 5,520,638 A | * | 5/1996 | O'Quinn et al. ................ 604/67 |
| 5,563,584 A | | 10/1996 | Rader et al. |
| 6,475,178 B1 | * | 11/2002 | Krajewski et al. ............. 604/31 |
| 6,497,680 B1 | * | 12/2002 | Holst et al. ..................... 604/153 |
| 6,855,122 B1 | | 2/2005 | Ohta et al. |
| 2003/0055375 A1 | * | 3/2003 | Holst et al. ....................... 604/67 |
| 2005/0245871 A1 | * | 11/2005 | Delnevo et al. ................ 604/126 |
| 2006/0272421 A1 | * | 12/2006 | Frinak et al. ..................... 73/710 |
| 2007/0271062 A1 | * | 11/2007 | Vanderveen et al. .......... 702/138 |
| 2008/0156092 A1 | * | 7/2008 | Boiarski ..................... 73/304 R |

FOREIGN PATENT DOCUMENTS

| | | |
|---|---|---|
| CA | 2 528 721 A1 | 12/2004 |
| DE | 37 02 609 C1 | 6/1988 |
| EP | 0 276 377 A2 | 8/1988 |
| EP | 1 319 417 A1 | 6/2003 |
| WO | 2005/065749 A1 | 7/2005 |

* cited by examiner

Primary Examiner — Adam Marcetich
(74) Attorney, Agent, or Firm — Pearne & Gordon LLP

(57) ABSTRACT

In an infusion circuit (1), a peristaltic pump (7) displaced the infusion fluid along a line (3), sourcing it from a batch container (2). When a weight sensor (5) detects an emptying of the batch container (2), the pump is halted. If on stopping the pump the pressure measured by a sensor (6) operating in an expansion chamber (4) does not drop in excess of a predetermined threshold with respect to a non-empty container (2), a non-secure situation is signalled, due to an excessive quantity of air in the expansion chamber.

17 Claims, 3 Drawing Sheets

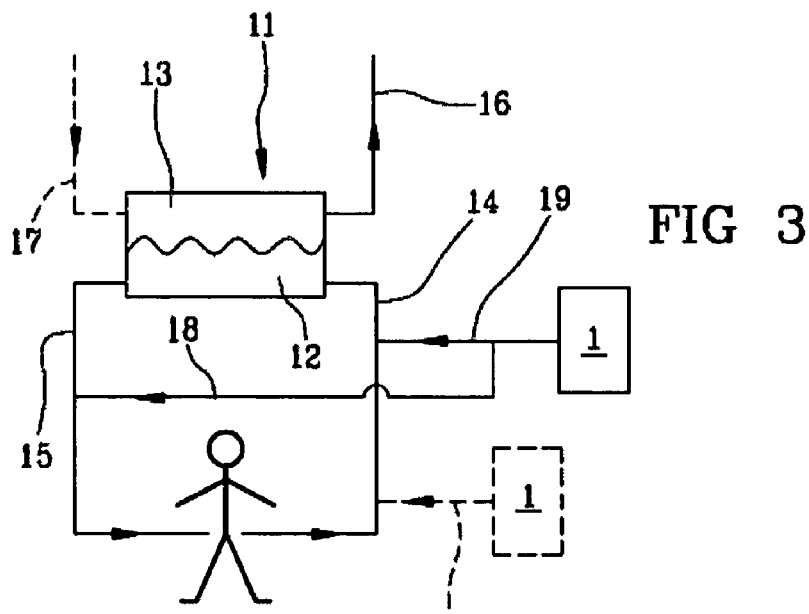
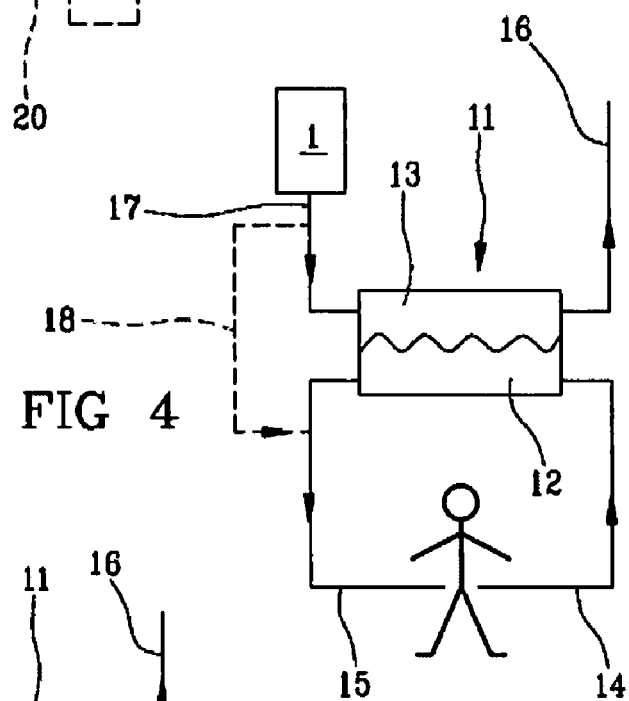
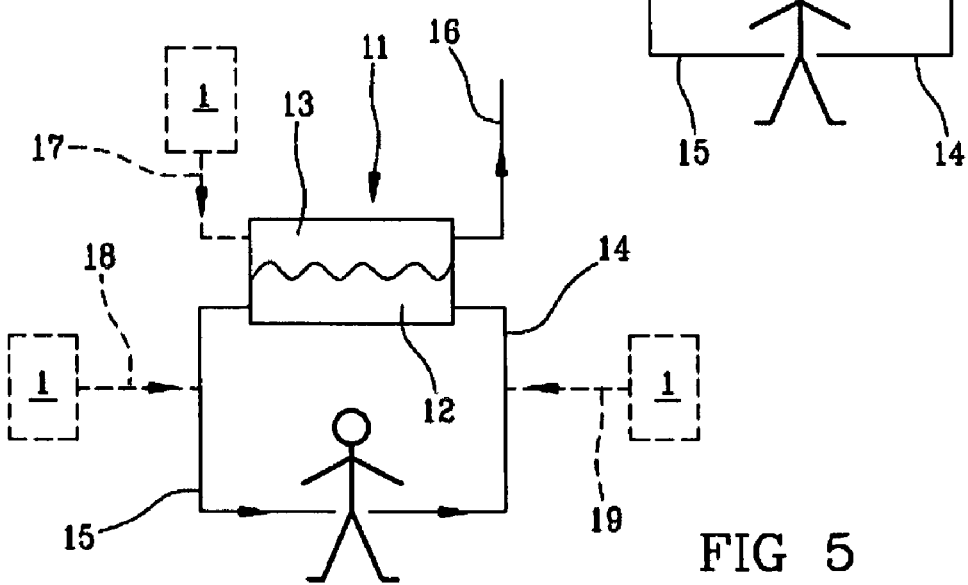
FIG 3
FIG 4
FIG 5

MEDICAL FLUID CIRCUIT COMPRISING A LOW LEVEL DETECTOR 1

BACKGROUND OF THE INVENTION

The invention relates to a medical fluid circuit and a control method of a medical fluid circuit.

Specifically, though not exclusively, the invention can be usefully applied in supplying a medical fluid, such as for example an infusion fluid or a dialysis fluid.

In particular, the medical fluid circuit of the invention comprises a source batch of the medical fluid which during use is emptied and has to be replaced by another, full source batch.

An infusion circuit is known which comprises an infusion pump that sources the infusion liquid from a batch container and sends it to an individual (directly into the body of the individual or via an extracorporeal blood circuit). Also known is using a monitoring system of the weight of the container used, for example a scales applied to the container. When the weight measured by the scales does not fall for a given period of time, the control unit of the infusion circuit signals that the container is empty and stops the infusion pump to prevent undesired air ingress into the infusion line.

There can however be a certain lapse of time after effective emptying of the container and the moment the infusion pump halts, during which time the infusion pump can draw air instead of infusion fluid into the infusion line. A certain quantity of air can therefore enter into an expansion chamber predisposed along the infusion line for degassing the infusion fluid via air-liquid separation. By effect of the introduction of air, the liquid level in the expansion/degassing chamber will diminish. When the operator intervenes to replace the empty container with another, full container, she or he normally controls that the liquid level in the expansion chamber is the desired level. If this is not the case, the operator adjusts the liquid level manually, for example by removing excess air from the expansion chamber by means of an aspirating syringe connectable to the expansion chamber.

A drawback of the prior art is the risk of having an excess of air in the infusion circuit on restarting the infusion fluid supply, after changing the batch container and following a missed control and intervention on the part of the operator.

The prior art comprises various medical fluid circuits which use a source batch of medical fluid.

WO 2005/065749 shows a system for detecting emptying of a container of an infusion fluid, in which an infusion line is provided with an expansion chamber in the form of a drip chamber, an infusion pump downstream of the expansion chamber and a pressure sensor between the expansion chamber and the infusion pump. The pressure sensor is used for recognising the emptying of the container.

U.S. Pat. No. 5,563,584 shows an infusion system with a monitoring device of the batch container level of an infusion liquid. The device comprises a pressure sensor arranged at the outlet of the container for receiving the pressure exerted by the liquid internally of the container. When the container is close to empty, the pressure drops below a certain threshold.

EP 1319417 shows an apparatus for monitoring a medical fluid system (for example an infusion or dialysis apparatus) in which a certain quantity of fluid is extracted from/injected into the system and the pressure difference in the system is measured before and after the extraction/injection. This difference is used to deduce some parameters which describe the situation of the system, such as for example the quantity of gas present in the system.

U.S. Pat. No. 6,855,122 shows an infusion system comprising a batch container of a substitution fluid, an expansion chamber in the form of a drip chamber, a pump and a fluid-empty sensor arranged between the container and the pump.

SUMMARY OF THE INVENTION

An aim of the present invention is to provide a medical fluid circuit having a relatively low risk of supplying a fluid containing an excessive quantity of non-dissolved gases.

A further aim of the invention is to provide a method for monitoring a medical fluid circuit able to detect a situation in which there is an excess of non-dissolved gases in the circuit.

An advantage of the invention is that it guarantees prompt triggering of an alarm signal in a case in which a faulty situation of excess air in a medical fluid circuit is detected.

A further advantage is that it makes available a medical fluid circuit which is constructionally simple and economical.

A still further advantage is that it gives rise to a monitoring system for a medical fluid circuit which is able to signal, in a timely and reliable way, an undesired situation of excess of air in the circuit itself, in particular during a replacement of an emptied source batch of medical fluid with a full one.

These aims and others besides are all attained by the object of the invention as it is characterised in one or more of the claims.

In a specific embodiment of the invention, a control unit of a medical fluid circuit is programmed to perform a monitoring process of the circuit comprising the following stages: displacing a certain quantity of fluid along a medical fluid supply line, measuring the pressure in an expansion chamber arranged on the supply line during the displacement, and recognising a faulty situation of excessive air presence in the expansion chamber if the pressure does not sufficiently lower. The displacement of the medical fluid can be optionally realised by means of a positive displacement pump, such as for example a wall-deforming pump. The medical fluid can be removed from a source batch of the fluid itself. The medical fluid circuit can optionally comprise a device for signalling the emptying of the source batch; the device can in turn comprise, for example, a weight sensor connected to a container of the medical fluid.

In a specific embodiment of the invention, a medical fluid circuit comprises a source batch of fluid, an infusion pump for removing the fluid from the source, an expansion chamber for gas-liquid separation in the medical fluid, and a pressure sensor for measuring the pressure in the expansion chamber. When the source batch is empty, before stopping supply of the medical fluid (for example in order to be able to proceed to the replacement of the empty source batch with a full one), for a certain period of time the supply means (for example a pump of the medical fluid) cause a certain quantity of gassy fluid to enter the expansion chamber: if, during this time, the pressure measured in the expansion chamber falls relatively sharply (for example the pressure drop exceeds a certain threshold value), this means that the quantity of liquid in the expansion chamber is relatively high and it is therefore not necessary to perform any regulation of the liquid level in the chamber; if on the other hand the pressure measured in the expansion chamber does not drop by a sufficient amount (for example the pressure drop does not exceed a certain threshold value), this means that the quantity of gas in the expansion chamber is excessively high and an adjustment of the liquid level in the chamber will have to be made, for example by aspiration of gas with a syringe.

In a specific embodiment of the invention, a liquid level monitoring process comprises stages of monitoring the pressure in the expansion chamber over a determined period of time in which a source batch of the medical fluid is emptied, and calculating a faulty situation in the liquid level in the expansion chamber if the pressure drop during the above-cited determined time period does not exceed a predetermined threshold value.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will be made herein below with reference to the figures of the drawings, provided by way of non-limiting illustration, in which:

FIGS. 3 to 5 show three different applications of an infusion circuit such as the one in FIG. 1.

DETAILED DESCRIPTION

Figure 1:
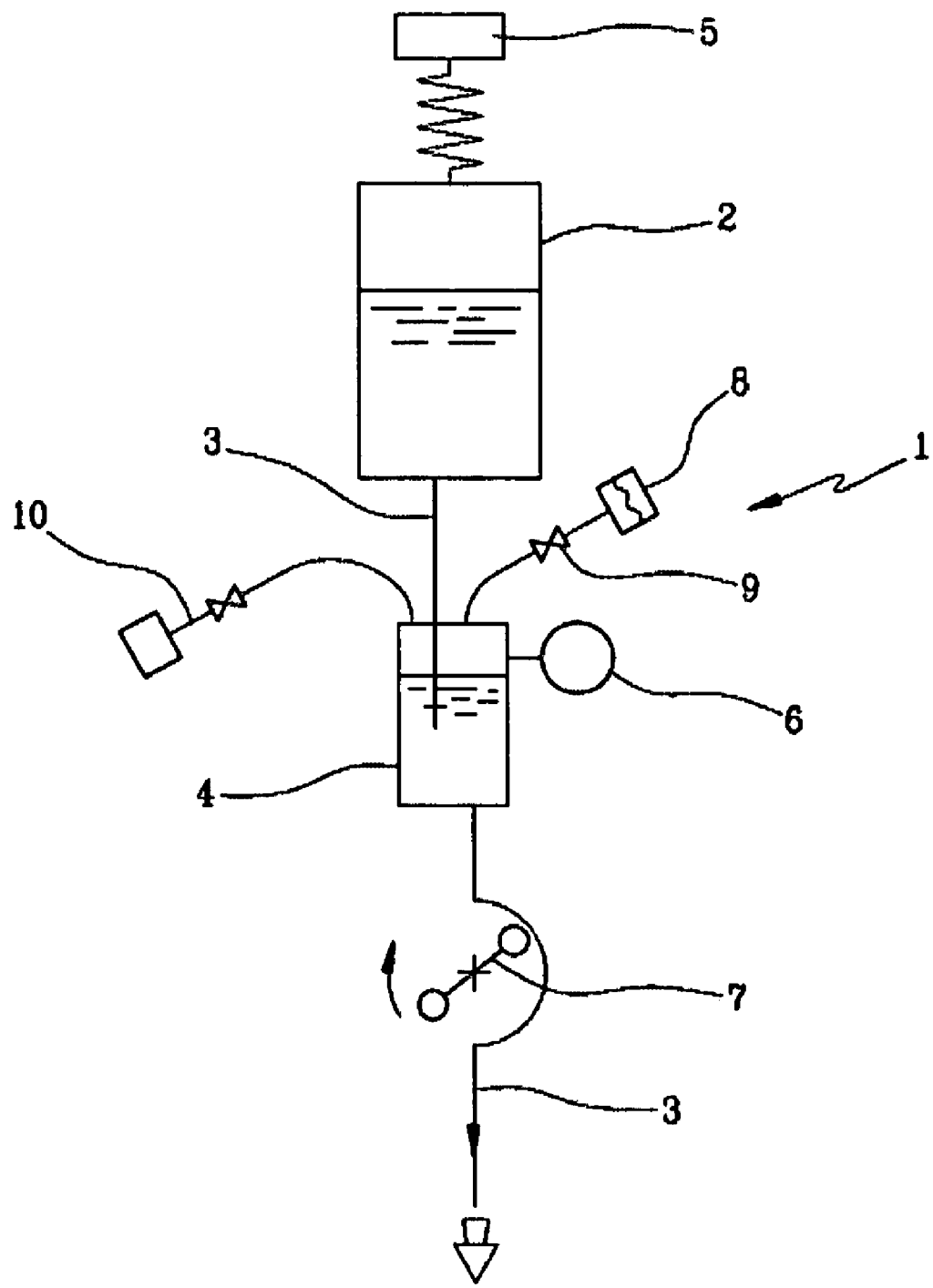
FIG. 1 is a first embodiment of an infusion circuit realised in agreement with the present invention.

In FIG. 1, 1 is denoted in its entirety by an infusion circuit, 2 denotes a batch container for an infusion fluid, 3 an infusion line, 4 an expansion chamber, 5 a weight sensor, 6 a pressure sensor, 7 an infusion pump, 8 a hydrophobic filter applied to a vent of the chamber 4, 9 a block valve (clamp), 10 a service line for access to the chamber 4 (for example by means of a syringe).

The infusion circuit 1 can be directly associated to a vascular access of an individual, for example by direct infusion of a medical fluid. The infusion circuit 1 can be used to infuse a medical fluid in an extracorporeal blood circuit removing blood from a vascular access of an individual and returning it after carrying out a treatment (for example dialysis, hemofiltration, hemodiafiltration, pure ultrafiltration, therapeutic plasma exchange, hemoperfusion, treatment for hepatic failure, removal of some blood components, separation of some blood components, etc.).

The infusion fluid can comprise, for example, any medication to be infused in a patient, a substitution fluid for a hemo (dia)filtration treatment, a buffer solution used in an extracorporeal blood treatment, an anticoagulant, etc.

The batch container 2 functions as a source of infusion fluid. The container 2 can comprise, for example, a flexible bag. The container 2 is, in the specific case, a bag with collapsible walls. The pressure inside the container 2 is, optionally, equal to the ambient pressure. It is possible to use a container having an inside thereof connected or connectable to the outside by means of a vent provided, for example, with a hydrophobic filter (with a configured clamp possibly provided, for example arranged on a service line connected to the container, for isolating the container from the outside environment, i.e. closing the vent.) A batch container could also be used which comprises a bag not having other connections with the outside (for example vents etc) apart from connections to the line 3, or a batch container not having vents or having a selectively-closable vent, for example closable by an operator.

In the specific case, the container 2 is sterilised and can be hermetically sealed from the outside environment in order to maintain sterility thereof. The container 2 can comprise any batch container of known type used in a medical application as a source of a medical fluid.

The infusion line 3 is connected to the batch container 2 in order to supply the infusion fluid. The infusion line can comprise an end provided with a removable connector (of known type and not illustrated) for connection with the container 2. The removable container can comprise, for example, a spike for perforating a perforable element such as to open a port and access fluid from the bag, or a connector (for example a luer connector) provided with a screw coupling for connection to a corresponding counter-connector borne by a fluid port connected to the container 2, or any other type of removable connector used in the medical field for sealed fluid connection. The removable connection enables an operator to change, rapidly and simply, a used container for a full container. It is possible to arrange a clamp or other blocking device (not illustrated) for closing the infusion line 3 during the change of container.

The expansion chamber 4 is arranged along an infusion line 3 for gas-liquid separation of the infusion fluid. Optionally the chamber 4 is configured to give rise, in use, to a liquid level that separates an upper part of gas accumulation and a lower part full of degassed liquid. It is also possible, for example in an initial stage of preparation and start-up of the circuit, to totally fill the gas-liquid separation chamber with liquid, the separation chamber having a hydrophobic element operating on the gas vent arranged in the upper part of the chamber which prevents outflow of liquid. The chamber 4 is further configured for the gas-liquid separation in a medical fluid which flows continuously from an inlet to an outlet of the chamber. The expansion chamber 4 can comprise any gas-liquid separation chamber used in a medical circuit. As mentioned, the chamber 4 can comprise a fluid inlet (arranged at an end of a first tract of infusion line 3 comprised between the container 2 and the chamber 4) and a fluid outlet (arranged at an end of a second tract of infusion line 3 comprised between the chamber 4 and the user). In the specific case the fluid inlet is arranged higher than the fluid outlet, with reference to a use configuration of the chamber 4 (in which, in the specific case, the vent is disposed high up). In the specific case both the fluid inlet and outlet are arranged at a lower height with respect to the liquid level desired in the chamber 4.

The weight sensor 5 is used to precisely control (in a known way) the flow of infusion fluid supply. The weight sensor 5 is also used to determine when the container 2 has emptied. In the specific case the sensor 5 is connected to a control unit (not illustrated) which periodically reads off the weight signal provided by the sensor 5 and which recognises that the container has emptied when the measured weight no longer falls (over a certain period of time). It is possible to provide other ways for determining that the container 2 is empty, such as for example determining when the value of the measured weight falls below a predetermined threshold which corresponds to the weight (known) of the empty container. It is further possible to provide other ways (of known type) which detect the emptying of the sensor, such as for example the use of level sensors which are operatively associated to the container 2, or moisture presence/absence sensors (for example sensors provided with an electrical resistance) arranged in proximity of the container outlet, or liquid presence/absence sensors (for example optical or ultrasonic sensors) arranged, for example, on the infusion line 3 in proximity of the container outlet 2, etc.

The pressure sensor 6 is configured to send signals indicating the pressure in the expansion chamber 4. The sensor 6 can comprise any one of the sensors of known type for measuring the pressure in a medical circuit, such as for example an impermeable and deformable membrane sensor (pressure pod), or a membrane transducer protector sensor (commonly called blood-catcher when used in a blood circuit), or another type. The pressure sensor 6 can be directly associated to the chamber 4, or can be arranged on the infusion line 3 in proximity of the chamber 4, or can be arranged on a service line (not illustrated) connected (for example in a branch line) with the chamber 4 or the infusion line 3 (to this end, the filter 8 could be used, for example, connected to a pressure transducer external of the circuit).

The infusion pump 7 can comprise, as in the specific case, a peristaltic pump (for example rotary) or another tube-deforming or other flexible-wall-deforming pump of known type (such as for example a membrane pump, a bellows pump, etc.). The infusion pump 7 can comprise, in particular, a volumetric pump (a positive displacement pump) usable in a medical circuit. The pump 7 is connected to the control unit in order to supply the infusion fluid. During normal operation, the control unit guides the pump 7 (with a retroactive control of known type) on the basis of weight signals received from the sensor 5 such as to batch the flow of infusion fluid. The pump 7 is further controlled such as to halt when the control unit recognises that the container 2 is empty.

The hydrophobic filter 8 comprises a hydrophobic membrane which enables passage of gas (air) and prevents passage of liquid (infusion fluid). The filter 8 is arranged, in the specific case, on an auxiliary line connected to the top of the expansion chamber 4. The filter 8 can be used, in particular, for enabling evacuation of gas during the first filling of the expansion chamber, such as to enable a desired liquid level to be created. For example, during the first filling the expansion chamber 4 is completely filled such that the liquid reaches the hydrophobic membrane. An incomplete filling can also be arranged. A clamp 9 (for example either manual or automatic) can also be predisposed to close the service line and isolate the filter 8 from the chamber 4. Optionally a service line 10 can be provided which can be used, for example, for (manual) resetting of the desired liquid level in the chamber 4 (for example by aspiration with a syringe connected to the free end of the line 10 with the aim of aspirating gas and thus raising the liquid level); the service line 10 is optionally provided with a closing clamp and a connector (for example a luer connector) arranged at a free end thereof.

The control unit is configured for performing a control procedure of the situation in the expansion chamber 4.

During normal functioning, the control unit commands the infusion pump 7 retroactively on the basis of a signal provided by the weight sensor 5 in order to provide a desired flow rate. During this stage, in normal conditions, the weight sensor 5 detects a certain weight drop (due to the activating of the pump, which removes the infusion liquid from the container 2) while the pressure sensor 6 detects a more-or-less constant pressure (about the same as the atmospheric pressure plus the pressure of the liquid head in the container 2) or, in other words, slightly decreasing as the liquid head progressively diminishes (even if in a practically insignificant way or nearly so). This situation is described on the left side of the graph of FIG. 2, with reference to the broken lines and the first part of the unbroken lines, up to points at which the straight lines have a change in inclination. The profile followed by the curve W of the weight can be linear but can also be curved, depending on the desired profile for the flow rate of the infusion fluid which is normally set by the operator or which, in certain cases, can be set automatically by the control unit on the basis of determined criteria which the operator can program. It is however quite usual for the profile of the curve W of the weight, and the curve P of the pressure too, to follow a smooth and regular mean progress (obviously, as is known, the values detected by the sensors in general oscillate about an effective value, due to various disturbances and errors which are intrinsically connected with the measuring instruments, and thus practically unavoidable).

During normal operation of the infusion apparatus, the separation chamber 4 is isolated from the external environment (atmosphere). The valve 9 and the valve on the service line 10 are closed. Any other vent and connection with the atmosphere is closed.

When (about the instant indicated by $T_v$ in FIG. 2) the container 2 is completely emptied of liquid or almost emptied (at times portions of liquid can stagnate in the folds of the flexible wall of the container 2 or in other zones, so that complete emptying can be uncertain and in any case not easily determined, the lines W and P, which up to that moment had followed a fairly smooth or regular linear progression (at least as regards the mean overall progression), are subject to a change in inclination. This change is, generally, very much more pronounced and easily detectable for the pressure curve P and much more difficult to detect (having a relatively insignificant entity which is thus comparable to the disturbances and errors associated to measuring instruments) for the weight curve W.

When the control unit detects that the weight reading provided by the sensor 5 is no longer dropping (about the instant indicated by $T_s$ in FIG. 2), it deduces that the container 2 is empty and therefore stops the pump 7. The empty container condition is normally detected by the control unit with a certain delay ($T_s$-$T_v$) with respect to the actual emptying. This delay normally means that the pump 7 causes a certain quantity of air contained in the container 2 to enter the infusion line 3 and also the expansion chamber 4. Normally, in the time interval $T_s$-$T_v$, starting from the emptying of the container 2 and before stopping the pump 7, the pressure measured by the sensor 6 drops fairly sharply. This drop can be due to various factors, among which in particular the absence of liquid head in the container 2 and also the reduction of the total quantity of liquid in the tract of infusion line 3 (including the expansion chamber 4) arranged upstream of the infusion pump 7, or other factors connected to the change in gas/liquid ratio in the volume defined by the expansion chamber 4.

The control unit examines the pressure progression provided by the sensor 6 up until halting the pump 7, and in particular it examines what happens in the time interval $T_s$-$T_v$: this progression is taken as indicative of the quantity of liquid present in the chamber 4. In particular, if it is detected that the pressure has dropped considerably, measured with respect to the measured pressure value in a situation in which the container 2 was not yet entirely emptied (this pressure value being, as mentioned, about the same—about atmospheric pressure—as the pressure value measured during all the normal infusion process, if it is not desired to take account of the slight drop due to the reduction of the liquid head in the container 2), this can mean that the quantity of liquid in the container 2 is relatively high, so that it is not necessary to reset the liquid level before newly infusing the infusion liquid. It is, in practice, possible, for example, to detect the pressure change in the time interval $T_s$-$T_v$, or to analyse a plurality of pressure values measured during that time interval.

If on the other hand the pressure, with respect to the full-container situation, has been subject to a relatively small drop, it means that the quantity of air in the chamber 4 is relatively high (i.e. that the liquid level is low, as the volume of the chamber 4 is constant and predefined), so it might be necessary to reset the desired liquid level, for example by means of manual aspiration of a certain quantity of air from the chamber 4, using a syringe.

Figure 2:
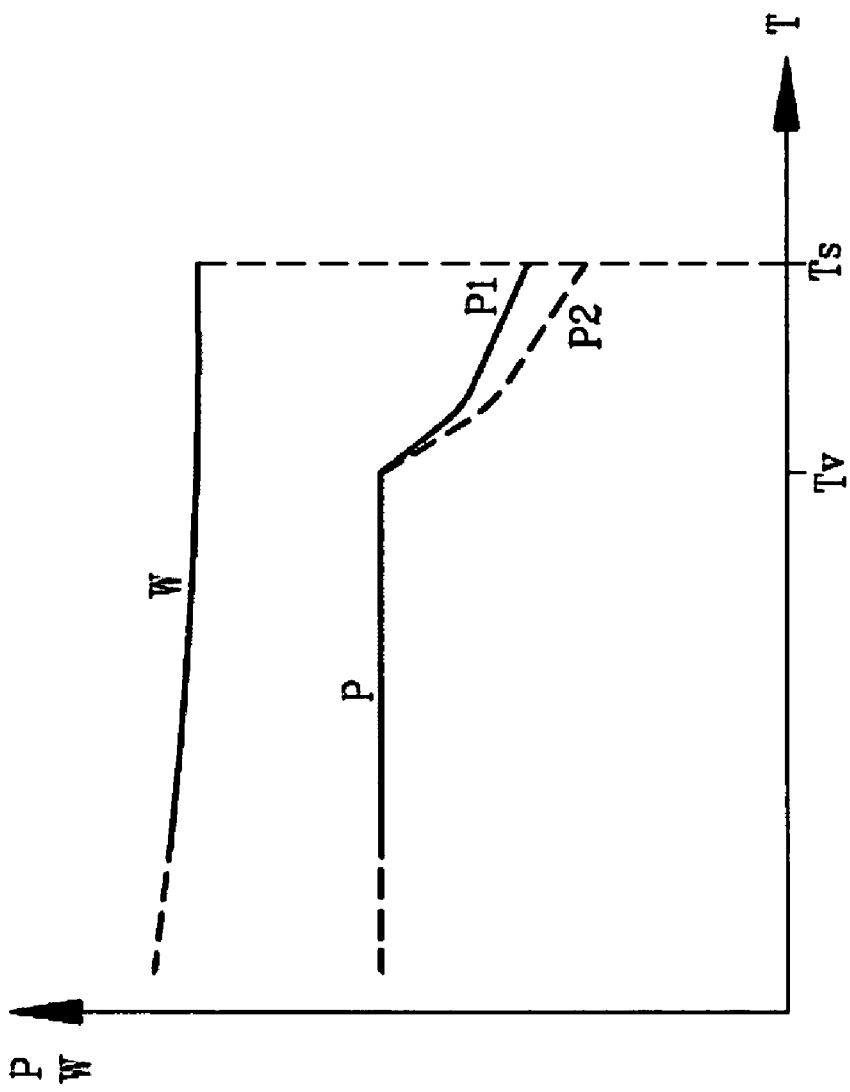
FIG. 2 is a graph which schematically indicates the change over time of the weight W of the source batch 2 and the pressure P in the expansion chamber 4, comprising a time interval over which the container has been emptied.

FIG. 2 illustrates, schematically and for reasons of comparison, both the pressure progression with a relatively low liquid level (curve $P_1$), i.e. in a condition of poor security of the fluid circuit on restarting the infusion, and the pressure progression with a relatively high liquid level (curve $P_2$), i.e. in a high-security condition.

In substance, by analysing pressure progression P over a time period (for example $T_s$-$T_v$) immediately preceding the halting of the pump 7 (for example by calculating the derivative of the pressure on the halting of the pump 7, or the change in pressure over a certain time interval preceding the halting of the pump 7, or over a time interval following the moment in which the pressure sharply changes, etc.), or simply on the basis of the pressure level in the chamber 4 on the halting of the pump 7, or on the basis of the difference between the pressure value immediately following the sharp pressure change and the final value on halting the pump etc., it is possible to deduce indications of the situation in the chamber 4, in particular on the volume of gas in the expansion chamber 4 and/or on the volume of liquid in the chamber 4 and/or on the ratio between the volume of gas and liquid in the chamber 4 and/or on the liquid level in the chamber 4.

FIG. 2, as mentioned above, schematically illustrates the qualitative progression over time of the pressure P measured by the sensor 6 and the weight W measured by the sensor 5, in the time period preceding the halting of the pump 7, i.e. in a time period comprising the moment (about $T_v$) of emptying of the container 2. As long as the container 2 still contains infusion fluid, i.e. it is not yet entirely emptied, the weight W drops according to the desired profile (for example by following a straight line which is slightly inclined downwards, if the operator had set a constant infusion fluid flow rate), and pressure P is practically constant (the pressure drop due to the reduction of the liquid head in the container 2 being practically irrelevant) and about the same as atmospheric pressure, i.e. the pressure acting on the container 2 with flexible and collapsible walls. When the container 2 is empty, the pressure P starts dropping sharply, while the weight W tends to assume a constant profile (as mentioned the constancy of the weight W can be disturbed, in this stage, by stagnating liquid zones which are dried up later, or other irregularities or unforeseen circumstances). After a certain period of time (which can depend on various factors, such as the sensitivity and precision of the weight sensor 5, the sampling time of the weight value, the structure and arrangement of the container 2 and the infusion line 3 connected thereto, etc.), the control unit calculates that the container 2 is empty and halts the pump (at time $T_s$).

As mentioned, FIG. 2 shows, with an unbroken line, the possible progression of the pressure $P_1$ in a case in which the liquid level in the chamber 4 is relatively low (low security situation), and with a broken line shows the pressure $P_2$ in a case of a relatively higher level (situation of greater security).

The pressure analysis P in the chamber 4 in the time period in which the weight W of the container 2 is about constant thus provides an indication of the state of fullness of the liquid in the chamber 4.

The control procedure performed by the control unit can comprise the following operations: detecting from the weight signal the emptying of the batch container 2; reading one or more pressure values in the expansion chamber 4 after the pressure has been subject to a sharp drop by effect of the emptying of the container 2; checking whether the pressure value or values are in a determined relation with at least a reference value (for example verify whether the difference between the pressure before the sharp drop and the pressure on halting the pump is greater or less than a threshold value); recognising a faulty situation on the basis of the above-mentioned verification (for example recognising a too-low liquid level in the chamber 4 if the above-mentioned pressure difference has not exceeded the predetermined threshold value).

The reference value or values which are used in the above verification can be established by taking account of various parameters or characteristics of the infusion system, such as for example the pump velocity during the time period in which the container is emptied and/or the fluid volume displaced by the pump during this time and/or the overall volume of the expansion chamber 4 and/or the time itself, etc. It is possible to calculate, for example, the volume of undissolved air present in the chamber 4 and therefore the liquid volume, using the gas law, on the basis of the fluid volume displaced in a certain time period, the pressure difference measured during the same time period and the overall volume of the expansion chamber 4.

The monitoring procedure can comprise, optionally, determining a pressure change in the expansion chamber 4 during a change in a predetermined parameter (for example one or more of the following parameters: time, fluid volume entering the expansion chamber 4, displacement of a mobile organ of an actuator configured for moving a fluid along the infusion line 3, the volume of a fluid displaced along the infusion line 3) and verifying whether the above-mentioned change in pressure is in a determined relation with at least a reference value (for example a pressure drop which, on the basis of calculations or empirically, identifies a limit situation in relation to the quantity of gas present in the chamber 4). The procedure can include signalling an anomalous situation if the above-mentioned pressure change is lower than a predetermined threshold value.

The monitoring procedure comprises, as mentioned, the detecting of an emptying situation of the container 2 by means of reading off at least a weight value of the container 2 itself. In particular at least two weight values of the container 2 can be read off, with a check being run on whether these weight values are in a determined relation with at least a reference value, such as for example whether their difference is around zero.

In other embodiments of the invention, instead of the infusion circuit 1 a dialysis circuit could be provided, comprising: instead of a batch container 2 for an infusion fluid, a batch container for a fresh dialysis fluid; an expansion chamber arranged along the fresh dialysis fluid supply line; a weight sensor operatively associated to the container of the dialysis fluid; a pressure sensor for measuring the pressure in the dialysis fluid expansion chamber (any sensor of known type used in a medical circuit); instead of an infusion pump, a fresh dialysis fluid supply pump (for example a positive displacement pump, a volumetric pump, a flexible-wall deformation pump, a peristaltic pump, etc.). In this case the dialysis circuit will comprise also a fluid chamber of a dialyser and a used dialysis fluid discharge line. The dialysis circuit now described might be used, for example, in an apparatus for intensive treatment of kidney failure.

In FIGS. 3 to 5, various apparatus for extracorporeal blood treatment are illustrated, which use the fluid circuits described herein. These apparatus comprise, in particular, various types and configurations of hemodialysis apparatus, hemofiltration apparatus and hemodiafiltration apparatus.

In FIG. 3, 11 denotes a membrane blood device, 12 a blood chamber of the device 11, 13 a fluid chamber separated from the blood chamber by means of a semi-permeable membrane, 14 an arterial line for removing blood from an individual, 15 a venous blood return line to the individual, 16 a used fluid discharge line, 17 an (optional) fresh fluid supply line, 18 a post-infusion line, 19 a pre-infusion line, 20 an (optional) further pre-infusion line. The post-infusion line 18 is connected to the venous line 15, i.e. downstream of the treatment device 11, while the pre-infusion line 19 is connected to the arterial line 14, i.e. upstream of the device 11. The post-infusion line 18 and the pre-infusion line 19 branch off from an infusion line connected to the outlet of the medical fluid circuit 1; one or the other of the post-infusion 18 and pre-infusion 19 lines might not be present or active, or both lines 18 and 19 can be present/active but separated from one another and each connected to the outlet of a respective fluid circuit 1. In a case in which the lines 18 and 19 branch off from a common branch-off point, it is possible to use a system of one or more valves for control (open/close) of the lines 18 and 19. The apparatus of FIG. 3 can be a hemodiafiltration apparatus (in pre-dilution and/or post-dilution) or, if the supply line is present and active, a hemodiafiltration apparatus. The post-infusion line 19 can operate alternatingly or contemporaneously with the pre-infusion line 19, for example by means of the use of a valve system which opens/closes the lines 18, 19 selectively, or by means of a fluid-displacing pump (for example a peristaltic pump) which operates on the pre-infusion line 18 or the post-infusion line 19.

In FIG. 4 the elements which are the same as in FIG. 3 have been denoted using the same numbers. The apparatus of FIG. 4 has a supply line 17 connected to the outlet of the medical fluid circuit 1. The supplied fluid can comprise, for example, a dialysis fluid or a substitution fluid. The (optional) post-infusion line 18 is branched off from the supply line 17. A pre-infusion line can be added or can replace the post-infusion line 18. The supply line 17 can operate alternatingly or simultaneously with the post-infusion line 18 (or pre-infusion line), for example by means of use of a valve system which selectively opens/closes the supply line 17, the post-infusion line 18 and/or the pre-infusion line, or by means of a fluid movement pump (of known type and not illustrated, for example a peristaltic pump) operating on the supply line 17 or on the post-infusion line 18, or by means of two pumps operating on two lines selected from the supply line 17, the post-infusion line 18 or the pre-infusion line.

Also in FIG. 5 the same elements as those of FIG. 3 are denoted using the same reference numbers. Here the fluid supply lines 17, 18, 19 are each connected to a respective fluid circuit 1 realised according to the invention. The lines 17, 18, 19 and/or the respective connection to the fluid circuit 1 are each optional. It is therefore possible to have only one or two (any one or two) or all three—from lines 17, 18, 19 present, and/or one or two (any one or two), or all three—from the connections to the respect fluid circuit 1.

It is further possible for the fluid circuit 1 to be an infusion circuit directly connected to an individual.

In other embodiments, and mainly with the aim of determining whether the chamber 4 of the above-described embodiments is full of the appropriate quantity of liquid, a level sensor can be provided (alternatively to or in addition to the pressure sensor 6 of the above-described embodiments) to indicate the liquid level in the chamber 4. The sensor is configured such as to provide a direct indication of the quantity of liquid in the chamber 4 (the sensor can, for example, issue a signal which is proportional to or indicative of the liquid level), such as to recognise and/or discriminate, on the basis of comparison with a reference value (for example a minimum level threshold), the condition of security or non-security.

As mentioned, the batch container 2 can be fluidly isolated from the outside environment, and can also be provided with a vent for fluid connection with the outside environment. In the latter case the first sensor 5 can comprise, in addition or alternatively to a weight sensor, a liquid level sensor (of known type) of the container 2.

The invention claimed is:

1. An extracorporeal blood treatment apparatus, comprising:
 a membrane exchanger for an extracorporeal blood treatment comprising a blood chamber and a fluid chamber, separated from one another by a semipermeable membrane;
 an extracorporeal blood circuit connected to the blood chamber; and
 a medical fluid circuit configured for infusing the medical fluid in the blood circuit or in the fluid chamber, the medical fluid circuit comprising:
  a batch container for a medical fluid;
  a fluid supply line connected to the batch container for supplying the medical fluid;
  an expansion chamber arranged along the supply line;
  a first sensor configured to send at least a first signal indicating an emptying of the batch container;
  a second sensor configured to send at least a second signal indicating a parameter in the expansion chamber, the parameter being a pressure in the expansion chamber; and
  a control unit configured to perform a control procedure of a situation in the expansion chamber, the control procedure comprising following operations:
   detecting a situation of emptying of the batch container from the first signal;
   detecting at least a value of said parameter inside the expansion chamber during the emptying situation;
   performing a control on whether the at least a value of the parameter is in a determined relation with at least a reference value, comprising determining a variation in the parameter in the expansion chamber during a variation of a further predetermined parameter, and controlling whether the variation of the parameter is in a determined relation with at least a reference value;
   recognising a faulty situation of a too low liquid level in the expansion chamber based on said control, wherein the faulty situation is recognised if the variation in the parameter does not exceed a predetermined threshold value.

2. The circuit of claim 1, wherein the control procedure comprises detecting at least two values of the parameter in the expansion chamber during the emptying situation, and controlling whether the at least two values of the parameter are in a determined relation with at least a reference value.

3. The circuit of claim 1, wherein the further predetermined parameter comprises a parameter selected from a group of parameters as follows: time, volume of a fluid entering the expansion chamber, displacement of a mobile organ of an actuator configured to move a fluid along the supply line, volume of a fluid moved along the supply line.

4. The circuit of claim 1, wherein the faulty situation is recognised if the variation in the parameter exceeds the predetermined threshold value.

5. The circuit of claim 1, wherein the faulty situation is recognised if the variation of the parameter is lower than the predetermined threshold value.

6. The circuit of claim 1, comprising an actuator configured to move the medical fluid along the supply line.

7. The circuit of claim 6, wherein the actuator is arranged on the supply line downstream of the expansion chamber.

8. The circuit of claim 6, wherein the actuator comprises a positive displacement pump.

9. The circuit of claim 1, wherein the first sensor comprises a weight sensor.

10. The circuit of claim 9, wherein the detecting an emptying situation comprises reading at least a weight value of the batch container and verifying whether the weight value is in a determined relation with at least a reference value.

11. The circuit of claim 9, wherein the reading an emptying situation comprises detecting at least two weight values of the batch container and controlling whether the weight values are in a determined relation with at least a reference value.

12. The circuit of claim 1, wherein the batch container is fluidly isolated from an outside environment.

13. The circuit of claim 1, wherein the batch container is provided with a vent for fluid connection with the outside environment, and in which the first sensor comprises a level sensor of the batch container.

14. An extracorporeal blood treatment apparatus, comprising:
- a membrane exchanger for an extracorporeal blood treatment comprising a blood chamber and a fluid chamber, separated from one another by a semipermeable membrane;
- an extracorporeal blood circuit connected to the blood chamber;
- a medical fluid circuit configured for infusing the medical fluid in the blood circuit or in the fluid chamber, the medical fluid circuit comprising:
  - a batch container for a medical fluid;
  - a fluid supply line connected to the batch container for supplying the medical fluid;
  - a pump to move fluid on the fluid supply line;
  - an expansion chamber arranged along the supply line;
  - a first sensor configured to send at least a weight signal indicating an emptying of the batch container;
  - a second sensor configured to send at least a pressure signal indicating a pressure in the expansion chamber;
  - a control unit configured to perform a control procedure of a situation in the expansion chamber, the control procedure comprising following operations:
    - detecting when the container is completely emptied of liquid or almost emptied by detecting that the weight reading provided by the first sensor is no longer dropping,
    - stopping the pump,
    - examining a pressure progression provided by the second sensor up until halting the pump, and taking this progression as indicative of the quantity of liquid present in the chamber,
    - recognising a faulty situation of a too low liquid level in the expansion chamber based on said examining, wherein the faulty situation is recognised if an absolute value of the pressure progression does not exceed a predetermined threshold value.

15. The apparatus of claim 14, wherein examining the pressure progression comprises calculating the derivative of the pressure on the halting of the pump.

16. The apparatus of claim 14, wherein examining the pressure progression comprises calculating the change in pressure over a certain time interval preceding the halting of the pump.

17. The apparatus of claim 14, wherein examining the pressure progression comprises calculating the difference between the pressure value immediately following a sharp pressure change and a final pressure value on halting the pump.

* * * * *